(12) United States Patent
Weese et al.

(10) Patent No.: US 11,886,543 B2
(45) Date of Patent: Jan. 30, 2024

(54) INTERACTIVE ITERATIVE IMAGE ANNOTATION

(71) Applicant: KONINKLIJKE PHILIPS N.V., Eindhoven (NL)

(72) Inventors: Juergen Weese, Norderstedt (DE); Thomas Blaffert, Hamburg (DE); Tom Brosch, Hamburg (DE); Hans Barschdorf, Dassendorf (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 369 days.

(21) Appl. No.: 17/294,731

(22) PCT Filed: Nov. 15, 2019

(86) PCT No.: PCT/EP2019/081422
§ 371 (c)(1),
(2) Date: May 18, 2021

(87) PCT Pub. No.: WO2020/104301
PCT Pub. Date: May 28, 2020

(65) Prior Publication Data
US 2022/0019860 A1 Jan. 20, 2022

(30) Foreign Application Priority Data
Nov. 22, 2018 (EP) .................................. 18207896

(51) Int. Cl.
*G06F 18/21* (2023.01)
*G06N 20/00* (2019.01)
(Continued)

(52) U.S. Cl.
CPC ...... *G06F 18/2178* (2023.01); *G06F 18/2148* (2023.01); *G06F 18/40* (2023.01); *G06N 20/00* (2019.01); *G06V 2201/03* (2022.01)

(58) Field of Classification Search
CPC .... G06F 18/2178; G06F 18/148; G06F 18/40; G06N 20/00; G06V 2201/03; G16H 50/20
See application file for complete search history.

(56) References Cited

U.S. PATENT DOCUMENTS 7,885,463 B2 2/2011 Zhang et al.
8,422,775 B2 4/2013 Wang et al.
(Continued)

FOREIGN PATENT DOCUMENTS

| CN | 107004141 A | 8/2017 |
| WO | 2015048196 A1 | 4/2015 |
| WO | 2016195698 A1 | 12/2016 |

OTHER PUBLICATIONS

Sathya et al: "Comparison of Supervised and Unsupervised Learning Algorithms for Pattern Classification"; International Journal of Advanced Research in Artificial Intelligence, vol. 2, No. 2, Jan. 2013, pp. 34-38.

(Continued)

*Primary Examiner* — Bobbak Safaipour
*Assistant Examiner* — Wassim Mahrouka (57) ABSTRACT

A system and computer-implemented method are provided for annotation of image data. A user is enabled to iteratively annotate the image data. An iteration of said iterative annotation comprises generating labels for a current image data part based on user-verified labels of a previous image data part, and enabling the user to verify and correct said generated labels to obtain user-verified labels for the current image data part. The labels for the current image data part are generated by combining respective outputs of a label propagation algorithm and a machine-learned classifier trained on user-verified labels and image data and applied to image data of the current image data part. The machine-learned classifier is retrained using the user-verified labels and the image data of the current image data part to obtain a retrained machine-learned classifier.

20 Claims, 5 Drawing Sheets

(51) Int. Cl.
   *G06F 18/40* (2023.01)
   *G06F 18/214* (2023.01)

(56) References Cited

U.S. PATENT DOCUMENTS

| | | | |
|---|---|---|---|
| 9,002,055 | B2 | 4/2015 | Funayama et al. |
| 10,885,392 | B2 | 1/2021 | Znamenskiy et al. |
| 2017/0256052 | A1 | 9/2017 | Bhattacharya et al. |
| 2018/0061091 | A1 | 3/2018 | Wang |

OTHER PUBLICATIONS

Yimam et al: "Interactive and Iterative Annotaiton for Biomedial Entity Recognition"; 12th European Conference on Computer Vision, ECCV 2012, vol. 9250, Jan. 2015, pp. 347-357.

Zheng et al: "Integrating Semi-Supervised Learning Methods for Label Fusion in Multi-Atlas Based Image Segmentation"; Frontiers in Neuroinformatics, vol. 12:69, Oct. 2018, pp. 1-11.

Brosch: Foveal Fully Convolutional Nets for Multi-Organ Segmentation; SPIE Medical Imaging 2018, vol. 10574.

Cicek et al: "3D U-Net:Learning Dense Volumetric Segmentation From Sparse Annotation"; Jun. 2016, Computer Science, Computer Vision and Pattern Recognition, 8 Page Document.

DICE: "Measures of the Amount of Ecologic Association Between Species"; Ecology, 26, pp. 297-302.

PCT/EP2019/081422 ISR & Written Opinion, dated Feb. 4, 2020, 21 Page Document.

Lefkovits et al: "Comparison of Classifiers for Brain Tumor Segmentation"; International Conference on Advancements of Medicine and Health Care Through Technology, Oct. 20167 vol. 59, pp. 195-200, Springer Nature.

Pace et al:"Interactive Whole-Heart Segmentation in Congenital Heart Disease"; Med Image Comput Assist Interv, Oct. 2015, 9351, pp. 80-88.

Ronneberger et al: "U-Net: Convolutional Networks for Biomedical Image Segmentation"; arXiv:1505.04597v1, May 2015 8 Page Document.

Zhao et al: "An Overview on Interactive Medical Image Segmentation" Annals of the BMVA (7), 2013, pp. 1-22.

INTERACTIVE ITERATIVE IMAGE ANNOTATION

CROSS-REFERENCE TO PRIOR APPLICATIONS

This application is the U.S. National Phase application under 35 U.S.C. § 371 of International Application No. PCT/EP2019/081422, filed on Nov. 15, 2019, which claims the benefit of European Patent Application No. 18207896.4, filed on Nov. 22, 2018. These applications are hereby incorporated by reference herein.

FIELD OF THE INVENTION

The invention relates to a system and computer-implemented method for interactive image annotation, for example to delineate an anatomical structure in a medical image. The invention further relates to a computer-readable medium comprising instructions to perform a computer-implemented method.

The invention further relates to a workstation and imaging apparatus comprising the system, and to a computer-readable medium comprising instructions for causing a processor system to perform the computer-implemented method.

BACKGROUND OF THE INVENTION

Image annotation is widely used in various field, including but not limited to the medical field. In the latter example, image annotation is often used to identify anatomical structures in medical images, e.g., by delineating the boundaries of the anatomical structure, by labelling of the voxels enclosed by the boundaries, etc. Such image annotation is also referred to segmentation or delineation. Besides the medical field, there are also various uses for image annotation in other fields.

It is known to perform image annotation automatically. However, fully automatic image annotation is challenging and often does not produce the required accuracy. For example, in the medical field, clinical application such as radiotherapy planning, pre-operative planning, etc. may require a sufficiently accurate annotation to produce reliable results. In recent years, learning-based methods such as model-based segmentation or deep (machine) learning approaches have shown great promise for automatic image annotation. These methods, however, typically require large amounts of manually labeled data which is time consuming and laborious and thus expensive to obtain. In addition, pre-trained algorithms can only be provided for the most common clinical tasks, but there is a large variety of further tasks where image annotation needs to be performed efficiently and accurately.

It is also known to perform image annotation semi-automatically, e.g., in an interactive manner as described in "*Interactive Whole-Heart Segmentation in Congenital Heart Disease*" by Pace, D. F. et al., MICCAI 2015, pp. 80-88. Although this avoids the need for the large amounts of manually labeled data, such image annotation may be less accurate than a well-trained learning-based approach, and/or require more interaction time of the user compared to a learning-based approach which is trained on a sufficiently large amount of image data.

US 2018/061091A1 describes multi-atlas segmentation which applies image registration to propagate anatomical labels from pre-labeled atlases to a target image and which applies label fusion to resolve conflicting anatomy labels produced by warping multiple atlases. Machine learning techniques may be used to automatically detect and correct systematic errors produced by a host automatic segmentation method.

SUMMARY OF THE INVENTION

It would be advantageous to obtain a system and method which facilitates accurate annotation while needing less manually labeled data and/or require less interaction time of the user.

In accordance with a first aspect of the invention, a system is provided for annotation of image data. The system may comprise:

an input interface configured to access the image data to be annotated;
a user interface subsystem comprising:
a user input interface configured to receive user input data from a user input device operable by a user;
a display output interface configured to provide display data to a display to visualize output of the system;
a processor configured to, using the user interface subsystem, establish a user interface which enables the user to iteratively annotate the image data, wherein an iteration of said iterative annotation comprises:
the processor generating labels for a current image data part based on user-verified labels of a previous image data part;
via the user interface, enabling the user to verify and correct said generated labels to obtain user-verified labels for the current image data part;
wherein the processor is further configured to:
generate the labels for the current image data part by combining respective outputs of:
a label propagation algorithm which propagates the user-verified labels of the previous image data part to the current image data part, and
a machine-learned classifier for labeling of image data, wherein the machine-learned classifier is trained on user-verified labels and image data and applied to image data of the current image data part; and
retrain the machine-learned classifier using the user-verified labels and the image data of the current image data part to obtain a retrained machine-learned classifier.

A further aspect of the invention provides a computer-implemented method for annotation of image data. The method may comprise:

accessing the image data to be annotated;
using a user interface, enabling a user to iteratively annotate the image data, wherein an iteration of said iterative annotation comprises:
generating labels for a current image data part based on user-verified labels of a previous image data part;
via the user interface, enabling the user to verify and correct said generated labels to obtain user-verified labels for the current image data part;
wherein the labels for the current image data part are generated by combining respective outputs of:
a label propagation algorithm which propagates the user-verified labels of the previous image data part to the current image data part, and
a machine-learned classifier for labeling of image data, wherein the machine-learned classifier is trained on user-verified labels and image data and applied to image data of the current image data part; and retraining the machine-learned classifier using the user-verified labels and the image data of the current image data part to obtain a retrained machine-learned classifier.

A further aspect of the invention provides a computer-readable medium comprising transitory or non-transitory data representing instructions arranged to cause a processor system to perform the computer-implemented method.

The above measures provide an input interface for accessing image data to be annotated. For example, the image data may be a 2D or 3D medical image which comprises an anatomical structure which is to be segmented by annotation of image elements, such as pixels or voxels, of the image data.

An interactive and iterative annotation mechanism is established as follows. The image data is partitioned, either explicitly or implicitly, into image data parts such as image slices or image sub-volumes. These image data parts are annotated iteratively. During the iterative annotation, a previous image data part may contain user-verified labels providing an annotation of the previous image data part. A current image data part, e.g., representing an image data part following the previous image data part, is annotated as follows. Here, the term 'following' may refer to the current image data part being annotated in a 'following' iteration after the previous image data part, but also to the current image data part 'following' the previous image data part within the image data, e.g., by representing an adjacent image slice or in general there being a spatial and/or temporal (in case of spatial-temporal image data) relation between the previous and current image data part.

A label propagation algorithm is used to propagate the labels of the previous image data part to the current image data part. Such label propagation algorithms are known per se, e.g., from the publication of Pace et al. as cited in the background section, and typically use similarity in image data between the previous image data part and the current image data part to propagate the labels from the previous image data part to the current image data part. In addition, a machine-learned classifier is used which may be trained on user-verified labels and image data, for example the user-verified labels and image data of the previous image data part, or the user-verified labels of other image data, e.g., of a previous image. The machine-learned classifier is applied to the current image data part and thereby provides a labelling of the current image data part. The outputs of the label propagation algorithm and the machine-learned classifier are combined to obtain combined labels for the current image data part (also named 'generated labels').

Since such generated labels may be imperfect, the user is enabled to verify and correct the generated labels, e.g., using a user interface such as a Graphical User Interface (GUI), thereby obtaining the user-verified labels. Mechanisms for correcting labels are known per se in the field of image annotation.

In a following iteration of the iterative annotation, these user-verified labels may be used to generate the labels for the following image data part to be annotated. Specifically, the user-verified labels are propagated to the following image data part. Additionally, the machine-learned classifier is retrained using the user-verified labels and the image data of the current image data part. Here, the term 'retraining' includes both comprehensive retraining, but also a partial retraining of the machine-learned classifier. For example, if the machine-learned classifier is a neural network which is retrained after each image slice or image sub-volume, only select layers or nodes of the neural network may be retrained, for example to limit the computational complexity of the retraining. In other embodiments, the retraining may be performed between the iterative annotation of different image data, for example after having completed the iterative annotation of the image data. In a specific example, all user-corrected labels of all image data parts may be used together with the respective image data to retrain the machine-learned classifier.

Thereby, the user-verified labels are used to improve the machine-learned classifier for the following iteration or following image data. For example, if the image data represents a 2D or 3D medical image from a time-series of 2D or 3D medical images, the following image data to which the image annotation may be applied may be a following 2D or 3D medical image from said time-series.

The above measures effectively correspond to a specific combination of an interactive and iterative annotation mechanism, such as the one known from Pace et al., and a machine-learned classifier. The machine-learned classifier is periodically, e.g., between iterations of the interactive annotation or between different image data, retrained using automatically generated labels which have been verified, and if needed corrected, by a user. The user-verified labels thus represent additional training data for the machine-learned classifier which may become available over time by way of the iterative annotation and which may be used to retrain the machine-learned classifier. As such, the machine-learned classifier typically improves over time, e.g., with each iteration or with each image.

At the same time, the user does not need to provide all of the training data, but in fact may only need to verify and correct labels which were automatically generated. Namely, these labels are generated by propagating the labels of a previous image data part and by the machine-learned classifier as trained thus far. As the accuracy of the labeling by the machine-learned classifier gradually improves, the user may gradually need to provide fewer corrections. The iterative annotation may thus gradually become more automatic and require fewer user corrections.

In the above measures, the label propagation algorithm effectively deals with the machine-learned classifier having initially little or no training data, and thereby a relatively low accuracy, which may be (well) below that of the label propagation algorithm. The label propagation algorithm may thus initially ensure adequate automatic labeling and effectively serve as bootstrap for the automatic labeling, as otherwise the user would have to initially manually generate all labels. The above measures thereby facilitate accurate image annotation, in which the user's part in ensuring the accuracy by verifying and correcting labels is gradually reduced as the accuracy of the machine-learned classifier improves over time. The above measures further need less manually labeled data than a traditional machine learning approach where the user has to manually label all of the training data.

In the above and following, the labels 'current' and 'previous' are merely used to distinguish between the image data parts between different iterations of the annotation. Subsequent use of the 'current' image data part in retraining thus refers to the particular image data, without implying any other currentness. The phrasing "retrain the machine-learned classifier using the user-verified labels and the image data of the current image data part" is thus to be understood to refer to the part of the image data for which said user-verified labels were generated.

Optionally, the processor is configured to retrain the machine-learned classifier between iterations of the iterative annotation, or between the iterative annotation of different image data, e.g., different images or sets of images.

The processor may be configured to generate the labels for the current image data part by combining the respective outputs of the label propagation algorithm and the machine-learned classifier by weighting. For example, if the label propagation algorithm and the machine-learned classifier each provide a probability map or function, both outputs may be weighted, e.g., using a convex weighting function, to obtain a combined probability map or function which represents or provides the labels. In this respect, it is noted that a probability function may yield a probability map, e.g., indicating probabilities in a map-like format for respective image elements of the image data part to which the algorithm/classifier is applied.

Optionally, the processor is configured to adjust the weighting during the iterative annotation of the image data, or between the iterative annotation of different image data. The weighting between the label propagation algorithm and the machine-learned classifier may be adjusted during the iterative annotation of the image data, e.g., between iterations or between image data, e.g., between the iterative annotation of different images.

Optionally, the processor is configured to determine the weighting of the iterative annotation based on a metric quantifying an annotation accuracy of the label propagation algorithm and/or the machine-learned classifier. There exist metrics in the field of image annotation for quantifying the annotation accuracy, such as the DICE coefficient as described elsewhere in this specification. Such metrics may for example use the user-corrected labels as a 'ground truth', but it is also possible to generate application-specific metrics which do not rely on a ground truth to give a coarse indication of annotation accuracy. For example, there may be an expectancy that the annotation has a certain shape in view of the expected object shape. Significant deviations from this expected shape may be considered in such a metric as indicative of a lower annotation accuracy. By estimating the annotation accuracy of either or both of the label propagation algorithm and the machine-learned classifier, the weighting may be adjusted, for example by increasing a weighting of the respective output which is deemed by the metric to represent a higher annotation accuracy, relative to the other output which is deemed by the metric to represent a lower annotation accuracy. In a specific example, the weighting may be adjusted between iterations or between image data, e.g., between the iterative annotation of different images.

Optionally, the metric quantifies the annotation accuracy based on a difference between i) the output of the label propagation algorithm and/or the output of the machine-learned classifier and ii) the user-corrected labels. The user-corrected labels may be advantageously used as 'ground truth' for the metric. Namely, a large difference between a respective output and the user-corrected label may indicate a lower annotation accuracy compared to a small or no difference at all.

Optionally, the processor is configured to adjust the weighting by increasing a weighting of the output of the machine-learned classifier relative to the output of the label propagation algorithm. The relative weighting of the output of the machine-learned classifier may be increased based on the knowledge or assumption that the annotation accuracy of the machine-learned classifier improves over time.

Optionally, the processor is configured to start the weighting of the output of the machine-learned classifier at or substantially at zero at a start of the iterative annotation. The relative weighting of the output of the machine-learned classifier may be initially substantially zero based on the knowledge or assumption that the machine-learned classifier is undertrained and thus provides inadequate annotation accuracy. Initially, the generated labels may be primarily determined by the label propagation algorithm.

Optionally, the output of the label propagation algorithm and/or the output of the machine-learned classifier is a probability map, or one or more control points defining a contour. Although the iterative annotation is primarily described with reference to probability maps, this is not a limitation, in that also other types of annotation may be provided by label propagation and by machine-learned classifier. For example, the annotation may be a contour which is based on control points. A weighting of the contours provided by the label propagation algorithm and the machine-learned classifier may for example comprise weighting parameters defining the relative or absolute location and/or other aspects of the control points.

Optionally, the user interface enables a user to select or define an annotation task, and the processor selects one of a number of machine-learned classifiers based on the annotation task, for example from an internal or external database. Each machine-learned classifier may be intended to provide a task-specific labeling, for example to enable annotation of different types of anatomical structures, different clinical tasks, etc. During or after iterative annotation, the selected machine-learned classifier may be retrained based on the user-verified labels and the image data. Accordingly, over time, a number of machine-learned classifiers may be obtained which are better trained for respective annotation tasks.

It will be appreciated by those skilled in the art that two or more of the above-mentioned embodiments, implementations, and/or optional aspects of the invention may be combined in any way deemed useful.

Modifications and variations of the workstation, the imaging apparatus, the method and/or the computer program product, which correspond to the described modifications and variations of the system, can be carried out by a person skilled in the art on the basis of the present description.

A person skilled in the art will appreciate that the system and method may be applied to two-dimensional (2D), three-dimensional (3D) or four-dimensional (4D) image data acquired by various acquisition modalities such as, but not limited to, standard X-ray Imaging, Computed Tomography (CT), Magnetic Resonance Imaging (MRI), Ultrasound (US), Positron Emission Tomography (PET), Single Photon Emission Computed Tomography (SPECT), and Nuclear Medicine (NM). A dimension of the image data may relate to time.

BRIEF DESCRIPTION OF THE DRAWINGS

These and other aspects of the invention will be apparent from and elucidated further with reference to the embodiments described by way of example in the following description and with reference to the accompanying drawings, in which.

It should be noted that the figures are purely diagrammatic and not drawn to scale. In the figures, elements which correspond to elements already described may have the same reference numerals.

LIST OF REFERENCE NUMBERS

The following list of reference numbers is provided for facilitating the interpretation of the drawings and shall not be construed as limiting the claims.

020 data storage
022 data communication
030 image data
032 label data
060 display
062 display data
080 user input device
082 user input data
100 system for interactive iterative annotation
120 input interface
122 internal data communication
140 processor
142 internal data communication
144 internal data communication
160 memory
180 user interface subsystem
182 display output interface
184 user input interface
200 label image
210 image slice
220 propagation-based prediction function
230 neural network-based prediction function
240 combined prediction function
250 predicted label image
260 difference to ground truth labeling
300-302 prediction functions
310-312 derived labels
320-322 difference to ground truth labeling
400 image slice
410 ground truth slice labeling
420 propagation-based prediction function
425 propagation-based validity function
430 neural network-based prediction function
435 neural network-based validity function
500 method for interactive iterative annotation
510 accessing image data of to be annotated
520 generating labels
530 enabling user to verify and correct labels
540 retraining neural network
600 computer-readable medium
610 non-transitory data

DETAILED DESCRIPTION OF EMBODIMENTS

The following embodiments are described with reference to the medical field. However, the techniques described in this specification can also be applied in other technical fields where image annotation is desired or needed. Any references to 'medical image', 'anatomical structure', etc. are thus to be interpreted as equally applying to another type of image containing another type of object.

The machine-learned algorithm is, by way of example, a neural network. However, also other types of machine-learned classifiers may be used, including but not limited to Support Vector Machines (SVM), AdaBoost and Random Forest, see for example the publication '*Comparison of Classifiers for Brain Tumor Segmentation*' by L. Lefkovits et al., IFMBE Proceedings, Volume 59.

Figure 1:
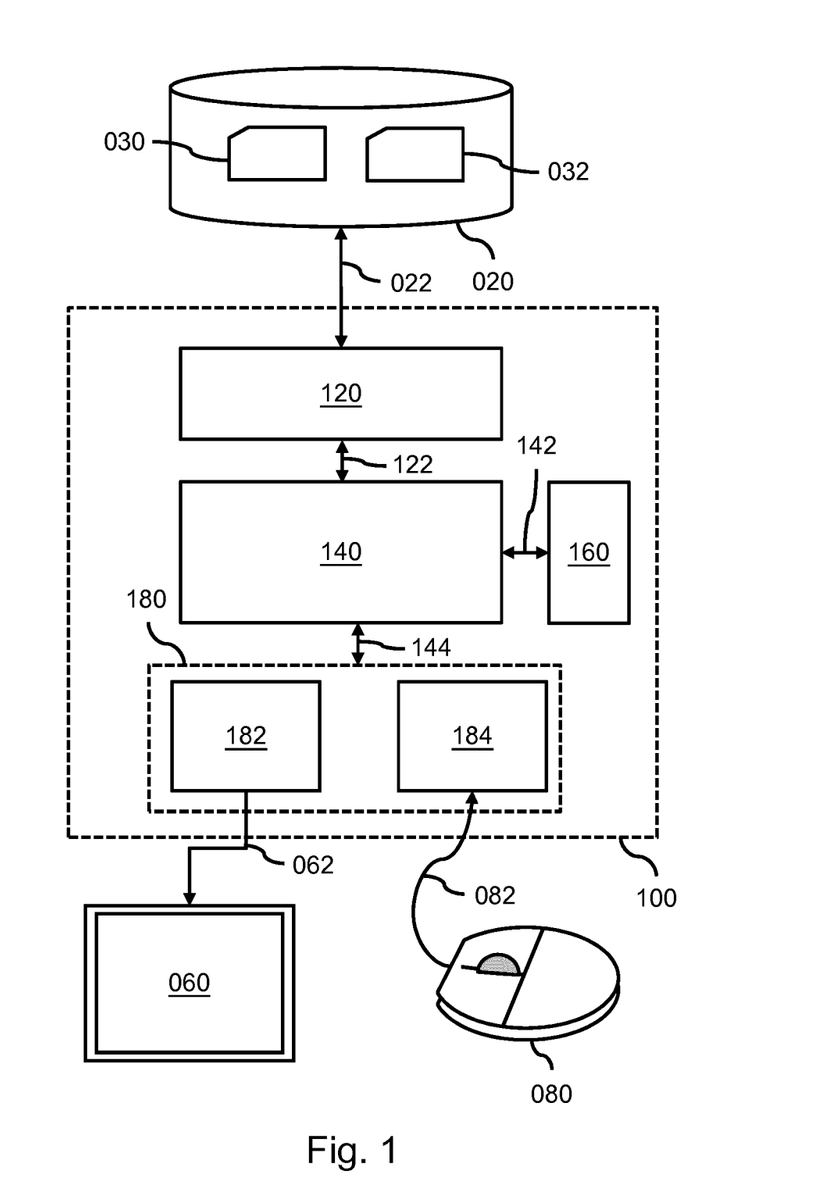
FIG. 1 shows a system for iterative annotation of image data, which comprises a user interface subsystem to enable a user to interact with the system during the iterative annotation, for example to verify and correct labels.

FIG. 1 shows a system 100 for annotation of image data. The system 100 comprises an input interface 120 configured to access image data. In the example of FIG. 1, the input interface 120 is shown to be connected to an external data storage 020 which comprises the image data 030. The data storage 020 may, for example be constituted by, or be part of, a Picture Archiving and Communication System (PACS) of a Hospital Information System (HIS) to which the system 100 may be connected or comprised in. Accordingly, the system 100 may obtain access to the image data 030 via external data communication 022. Alternatively, the image data 030 may be accessed from an internal data storage of the system 100 (not shown). In general, the input interface 120 may take various forms, such as a network interface to a Local Area Network (LAN) or a Wide Area Network (WAN), such as the Internet, a storage interface to an internal or external data storage, etc.

The system 100 is further shown to comprise a processor 140 configured to internally communicate with the input interface 120 via data communication 122, and a memory 160 accessible by the processor 140 via data communication 142. The processor 140 is further shown to internally communicate with a user interface subsystem 180 via data communication 144.

The system 100 is further shown to comprise a user interface subsystem 180 which may be configured to, during operation of the system 100, enable a user to interact with the system 100, for example using a graphical user interface. The user interface subsystem 180 is shown to comprise a user input interface 184 configured to receive user input data 082 from a user input device 080 operable by the user. The user input device 080 may take various forms, including but not limited to a computer mouse, touch screen, keyboard, microphone, etc. FIG. 1 shows the user input device to be a computer mouse 080. In general, the user input interface 184 may be of a type which corresponds to the type of user input device 080, i.e., it may be a thereto corresponding type of user device interface 184.

The user interface subsystem 180 is further shown to comprise a display output interface 182 configured to provide display data 062 to a display 060 to visualize output of the system 100. In the example of FIG. 1, the display is an external display 060. Alternatively, the display may be an internal display. It is noted that instead of a display output interface 182, the user interface subsystem 180 may also comprise another type of output interface which is configured to render output data in a sensory-perceptible manner to the user, e.g., a loudspeaker.

The processor 140 may be configured to, during operation of the system 100 and using the user interface subsystem 180, establish a user interface which enables the user to iteratively annotate the image data. Herein, an iteration of said iterative annotation comprises the processor 140 generating labels for a current image data part based on user-verified labels of a previous image data part, and via the user interface, enabling the user to verify and correct said generated labels to obtain user-verified labels for the current image data part. The processor 140 may be further configured to generate the labels for the current image data part by combining respective outputs of a label propagation algorithm which propagates the user-verified labels of the previous image data part to the current image data part, and a neural network for labeling of image data. The neural network may be trained on user-verified labels and image data and applied by the processor 140 to image data of the current image data part. The processor 140 may be further configured to retrain the neural network using the user-verified labels and the image data of the current image data part to obtain a retrained neural network. For example, such retraining may be performed between iterations, e.g., to obtain a retrained neural network for a subsequent iteration, or between different image data.

As a result of the iterative annotation of the image data 030, label data 032 may be obtained representing the annotation of the image data 030. The label data 032 may be stored by the system 100, e.g., in the data storage 020 or elsewhere, e.g., in association with the image data 030, or displayed to the user, etc.

This operation of the system 100, and various optional aspects thereof, will be explained in more detail with reference to FIGS. 2-4.

In general, the system 100 may be embodied as, or in, a single device or apparatus, such as a workstation or imaging apparatus or mobile device. The device or apparatus may comprise one or more microprocessors which execute appropriate software. The software may have been downloaded and/or stored in a corresponding memory, e.g., a volatile memory such as RAM or a non-volatile memory such as Flash. Alternatively, the functional units of the system, e.g., the input interface, the optional user input interface, the optional display output interface and the processor, may be implemented in the device or apparatus in the form of programmable logic, e.g., as a Field-Programmable Gate Array (FPGA). In general, each functional unit of the system may be implemented in the form of a circuit. It is noted that the system 100 may also be implemented in a distributed manner, e.g., involving different devices or apparatuses. For example, the distribution may be in accordance with a client-server model, e.g., using a server and a thin-client. For example, the (re)training may be performed by one or more servers, e.g., one or more cloud-based server(s) or a high-performance computing system.

It is noted that the label propagation algorithm and the neural network may be available to the processor 140 as respective data representations, e.g., as algorithm data and neural network data. Such data representations may for example be stored in and accessed from the memory 160 and/or the data storage 020.

The following embodiments described with reference to FIGS. 2-4 assume that the image data comprises a plurality of image slices. For example, the image data may be 3D image data which is natively partitioned in image slices, or such image slices may be generated, e.g., by multiplanar reformatting techniques. However, this is not a limitation, in that the following embodiments also apply to other partitionings of the image data into respective image data parts.

Very briefly speaking, the system 100 of FIG. 1 may enable a user to interactively annotate a 2D image slice of the 3D image data, for example using labels for foreground (e.g., the anatomical structure to be annotated) and background (the surroundings of the anatomical structure), or using different labels for different anatomical structures, or using different labels for different parts of an anatomical structure, etc. Such interactive 2D annotation may be performed using annotation tools as known from literature, e.g. as described in the publication "*Overview on interactive medical segmentation*" by Zhao, F.; Xie, X., Annals of the BMVA 2013, No. 7, pp. 1-22, which describes for example annotation tools enabling a user to interactively define a spline contour, with the spline contour being converted by the annotation tool into a corresponding region to which a label is applied, or a paint-brush tool for interactive label editing, or other more refined interaction methods. After annotating a 2D image slice, the annotation may then be propagated to a neighboring image slice, as also described in more detail with reference to FIGS. 2-4. The neighboring image slice may then be visualized with the annotation, and the user may again use the annotation tool to correct the annotation. This process may be repeated until all image data parts have been annotated, or at least a subset of the image data parts which the user wishes to annotate.

Figure 2:
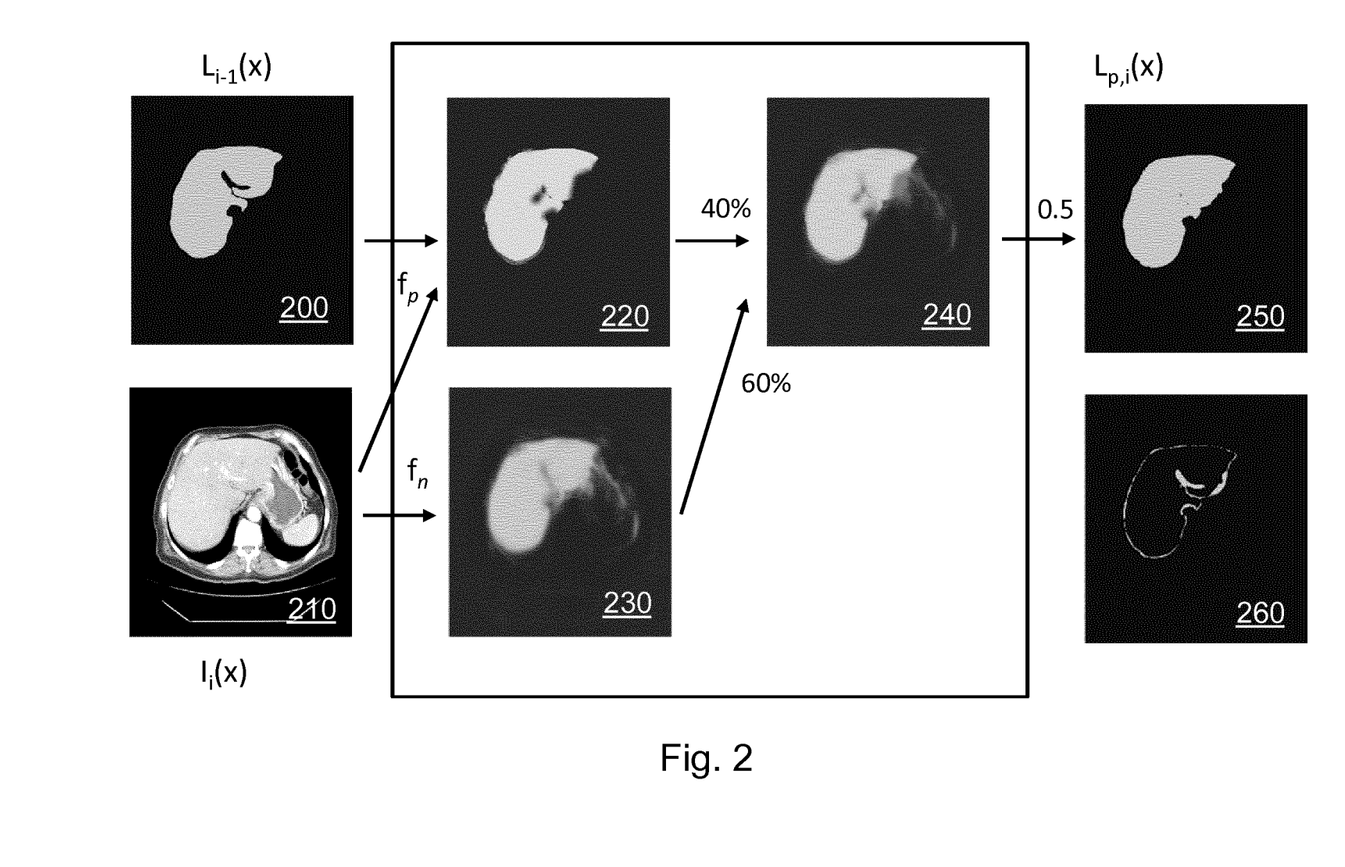
FIG. 2 illustrates an iteration of the iterative annotation.

FIG. 2 illustrates an iteration of the iterative annotation. Namely, when annotating an image slice $I_i(x)$ 210, a label propagation algorithm may be used to propagate labels $L_{i-1}(x)$ 200 to the current image slice. Here, $I_i(x)$ and $L_{i-1}(x)$ may be functions of the image coordinates x in slice i. The labels $L_{i-1}(x)$ may have been previously obtained for a neighboring image slice $I_{i-1}(x)$ (not shown explicitly in FIG. 2) by way of prediction and subsequent verification and correction by the user, and may be propagated to the current image slice $I_i(x)$ based on the similarity of image data in both image slices. The label propagation algorithm may for example be a 'mechanistic' label propagation algorithm as described in the publication of Pace et al. Here, the term 'mechanistic' may refer to a heuristically designed algorithm that for example does not rely on machine learning.

The label propagation may provide a prediction function 220. Moreover, if the neural network is already sufficiently trained, the neural network may be applied to $I_i(x)$ to provide a further prediction function 230. Both these prediction functions may for example be fuzzy label prediction functions, for example with values between 0 and 1. In the specific example of FIG. 2, these fuzzy labels may be a function $f_p(I_{i-1}(x), L_{i-1}(x), I_i(x))$ of the input image slices $I_{i-1}(x)$ and $I_i(x)$ and labels $L_{i-1}(x)$ for the patch-based label propagation, and a function $f_{n,i}(I(x))$ for the neural network prediction.

Both these prediction functions 220, 230 may be combined, e.g., by weighting, into a combined prediction function 240. For example, the combination may be a convex combination of both prediction functions 220, 230:

$$f_\alpha = f_n \alpha + f_p (1-\alpha)$$

in which the output of the neural network is weighted with a weighting factor $\alpha$ between 0 and 1. FIG. 2 shows a weighting with $\alpha=0.6$.

The combined prediction function 240 may be converted to predicted labels $L_{p,i}(x)$ 250, for example by applying a threshold of, e.g., 0.5 to the values of the combined prediction function 240. For example, any value below 0.5 may be assigned the label 'background', and any value of or above 0.5 may be assigned the label 'foreground', thereby obtaining the predicted labels $L_{p,i}(x)$ 250. The predicted labels $L_{p,i}(x)$ 250 may then be displayed to a user, whom may then verify and correct the labels. The thus-obtained user-verified and corrected labels Li(x) (not separately shown in FIG. 2) and image slice $I_i(x)$ 210 may be used to refine the neural network by performing a few training iterations using this data. FIG. 2 also shows a difference 260 of the predicted labels $L_{p,i}(x)$ 250 with a ground truth, being in this example here the user-verified and corrected labels.

Alternatively, the user-verified and corrected labels of a number of image slices, e.g., all image slices of the current image, may be used together to retrain the neural network, e.g., in case the user-verified and corrected labels of a single image slice do not represent sufficient training data for retraining.

Figure 3:
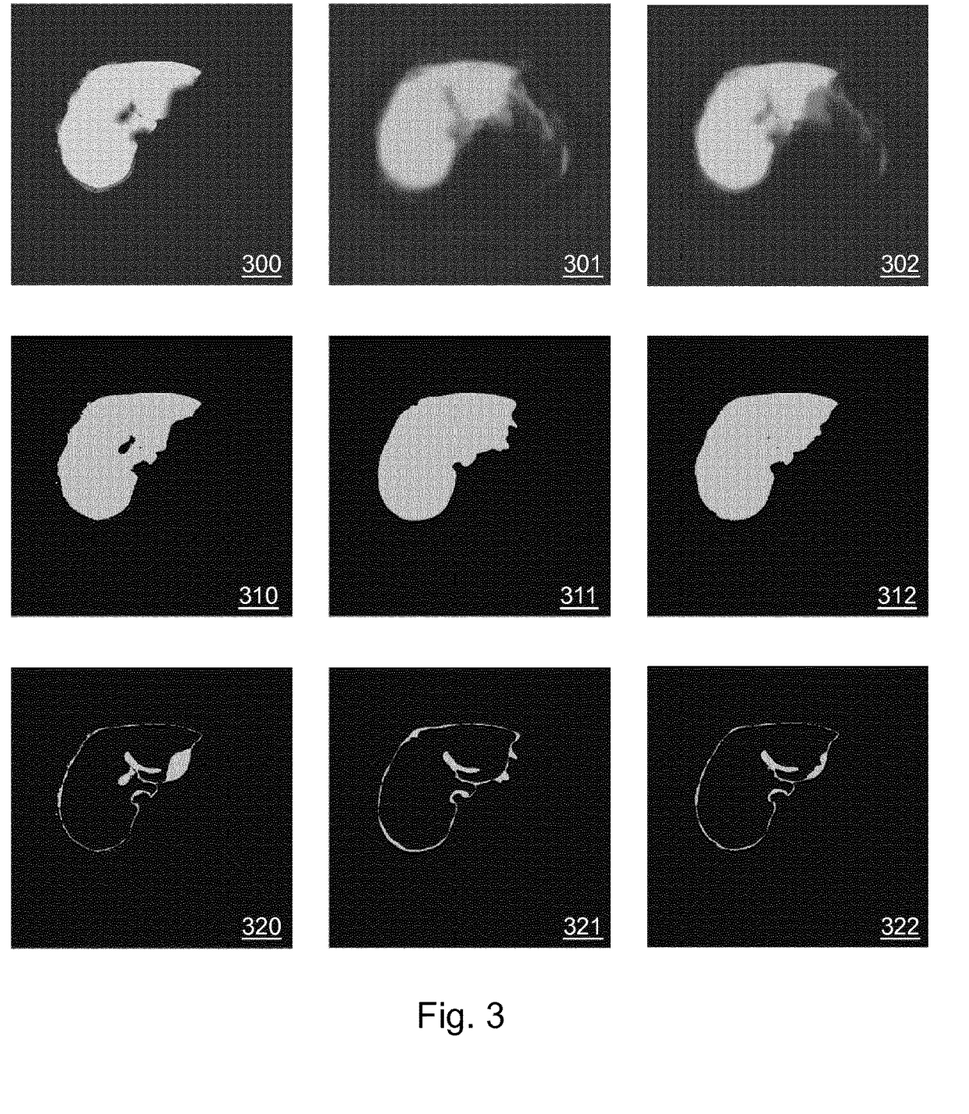
FIG. 3 shows prediction functions of a label propagation algorithm (left), a neural network (middle) and a 60%-40% weighted combination of both prediction functions (right), while further showing the labels which are generated based on the respective prediction functions and difference with respect to a ground truth labeling.

By way of example, FIG. 3 shows further prediction functions of a label propagation algorithm 300 (left column), a neural network 301 (middle column) and a 60%-40% weighted combination of both prediction functions 302 (right column), as well as the labels 310-312 which are generated based on the respective prediction functions 300-302 and their differences 320-322 with respect to a ground truth labeling. It can be seen that the prediction function 300 and labels 310 of the label propagation algorithm provide an 'under-segmentation' of the anatomical structure. By combining the prediction function 300 with the prediction function 301 of the neural network, an improved annotation of the anatomical structure is obtained, yielding a reduced difference 322 with respect to the ground truth labeling.

As neural network and training technique, any suitable neural network and training technique may be used, including but not limited to those described by "*U-net: Convolutional networks for biomedical image segmentation*" by Ronneberger, O.; Fischer, P.; Brox, T., MICCAI 2015, LNCS 9351, pp. 234-241, which is henceforth also simply referred to as 'U-Net', or "*Foveal fully convolutional nets for multi-organ segmentation*" by Brosch, T.; Saalbach, A., SPIE Medical Imaging 2018; SPIE Proc. 105740U, henceforth also simply referred to as 'F-Net'.

In general, there are many variants for training the neural network. For example, the neural network may be retrained on only the labels obtained in the current iteration, e.g., the user-verified and corrected version of $L_{p,i}(x)$ 250, and the associated image data part. Such retraining may be a partial retraining, which may also be referred to as 'refinement' of the neural network. Alternatively, the neural network may be retrained on all previous user-verified and corrected labels and associated image data parts. Such retraining may for example be performed after an interactive annotation session, e.g., in between different annotation sessions, or at night, etc. In some embodiments, the retraining may be performed by another entity than the entity providing the iterative annotation functionality. For example, the system may be represented by a workstation for providing the iterative annotation functionality and a server for retraining the neural network.

There are many ways to generate the weight for combining the outputs of the label propagation algorithm and the neural network. For example, before retraining the neural network using the current user-verified and corrected labels, the previous labels may be used to estimate the weight. For that purpose, annotated slices may be used as starting point and the annotation may be propagated to the next image slice using the label propagation:

$$f_{p,i}(x)=f_p(I_{i-1}(x),L_{i-1}(x),I_i(x))$$

resulting in a fuzzy label map with elements $0 \le f_{p,i}(x) \le 1$. $I_i(x)$ denotes slice i of the image I currently being annotated. $f_{p,i}(x)$ denotes the fuzzy label image and p denotes the label propagation algorithm. By applying a threshold t, the fuzzy label image may be converted into a label image:

$$L_i^t(x)=T(f_{p,i}(x),t)$$

Using the weight $\alpha$, the propagated fuzzy label image $f_{p,i}(x)$ may be combined with the fuzzy label image $f_{n,i}(x)$ generated with the neural network. The labels may be obtained by application of a threshold t, and a metric M that characterizes the annotation accuracy, such as the DICE value (also referred to as DICE coefficient) described in "*Measures of the amount of ecologic association between species*" by Dice, L. R., Ecology, 1945, volume 26(3), pp. 297-302, may be computed. The metric M may be summed over all image slices with user-verified and corrected labels, and an optimal value for the weight and the threshold may be obtained by maximizing the annotation accuracy:

$$(\alpha_{opt}, t_{opt}) = \underset{\alpha,t}{\mathrm{argmax}} \sum_i M(T((\alpha f_{n,i}(x) + (1-\alpha)f_{p,i}(x), t), L_i(x))$$

There are also many possibilities to combine the outputs of the label propagation algorithm and the neural network. For example, after having completed the annotation of a first and second slice of a new image, the weight $\alpha$ and threshold t may be optimized according to the above-described procedure to yield optimum results for the actual image at hand. This approach makes the neural network somewhat aware of its own performance: if the neural network encounters a familiar case, its weighting will increase, while in unfamiliar cases, its weighting will decrease and the labels are mainly obtained from the label propagation algorithm.

Instead of determining an optimal weight from previously annotated image data parts (e.g., previous image slices) or previously annotated image data (e.g., previous images), an empirical weight might be used that depends only or primarily on the number of previously annotated image data sets m, for example:

$$\alpha_m = e^{\frac{m}{20}}.$$

Alternatively, an empirical weight may be made dependent on the number of previously annotated image data parts, e.g., image slices.

In general, the weight may be chosen in dependence on previous values of the metric M (e.g., average metric for previous examples) obtained by label propagation ($M^P$) and the neural network ($M^N$). The weight $\alpha$ may be chosen to give a larger weight to the algorithm that provides the better segmentation result.

With respect to the fuzzy prediction functions, the following is noted. A fuzzy prediction function contains an implicit measure of certainty: if the value is close to 0 or 1, it may relatively certain that the derived labels are correct; however, if the value is closer to the threshold level, e.g., of 0.5, this certainty is low. This property may be used for a locally varying the mixing weight of the label propagation and the neural network prediction functions, which may be interpreted as a 'validity' of the decision function or a probability that the decision function is valid.

For example, validity functions may be defined as follows:

$$v_p=|2f_p-1|$$

$$v_n=|2f_n-1|$$

The validity functions may be a local combination weighting:

$$f_{vp} = f_p v_p + f_n (1 - v_p)$$

$$f_{vn} = f_n v_n + f_p (1 - v_n)$$

Figure 4:
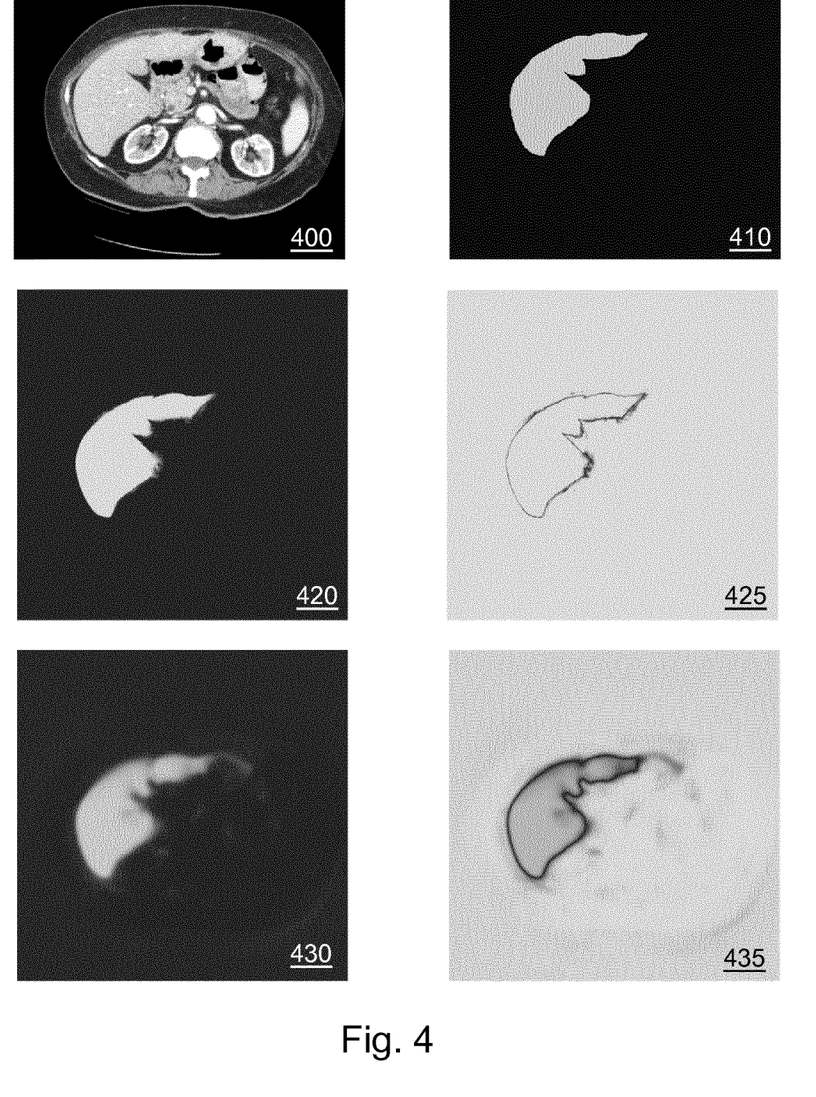
FIG. 4 illustrates a validity of the prediction functions of a label propagation algorithm and a neural network with respect to a ground truth labeling.

An example of validity functions is shown in FIG. 4 for an image slice 400, a ground truth slice labeling 410, a prediction function $f_p$ 420 provided by the label propagation algorithm, a prediction function $f_n$ 430 provided by the neural network, and the validity function $v_p$ 425 and the validity function $v_n$ 435.

The validity functions can be used and combined in various ways to construct the fuzzy label image. For example, both validity-weighted fuzzy label images are combined by a weight β:

$$f_\beta = f_{vn} \beta + f_{vp} (1 - \beta)$$

and the resulting function $f_\beta$ is combined with fa by a weight γ to the final fuzzy label image $f_\gamma$:

$$f_\gamma = f_\beta \gamma + f_\alpha (1 - \gamma)$$

with both β and γ between 0 and 1. Roughly speaking, α and β are the contribution of the neural network relative to the label propagation, and γ the contribution of the validity functions relatively to the weighting function.

Suitable mixing coefficients α, β, and γ may be obtained by the same optimization process as described for parameter optimization of label propagation. Since the neural network prediction function $f_n$ does not change during optimization, it may be implemented as lookup function. If all label propagation parameters were constant during the optimization of mixing coefficients, it would also be sufficient to calculate the label propagation prediction function $f_p$ once and use a lookup.

Figure 5:
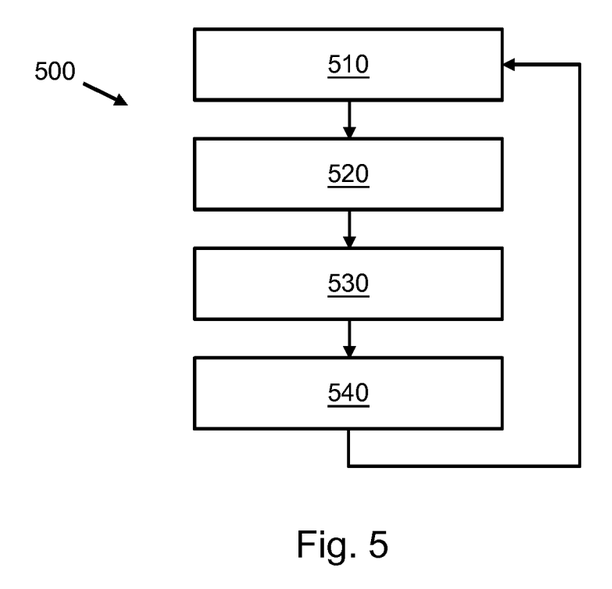
FIG. 5 shows a method for iterative annotation of image data.

FIG. 5 shows a block-diagram of computer-implemented method 500 for annotation of image data. The method 500 may correspond to an operation of the system 100 of FIG. 1. However, this is not a limitation, in that the method 500 may also be performed using another system, apparatus or device.

The method 500 may comprise, in an operation titled "ACCESSING IMAGE DATA OF TO BE ANNOTATED", accessing 510 the image data to be annotated. The method 500 may further comprise using a user interface, enabling a user to iteratively annotate the image data, wherein an iteration of said iterative annotation comprises, in an operation titled "GENERATING LABELS", generating 520 labels for a current image data part based on user-verified labels of a previous image data part, and in an operation titled "ENABLING USER TO VERIFY AND CORRECT LABELS", via the user interface, enabling 530 the user to verify and correct said generated labels to obtain user-verified labels for the current image data part. The method 500 may further comprise, in an operation titled "RETRAINING NEURAL NETWORK", retraining 540 the neural network using the user-verified labels and the image data of the current image data part to obtain a retrained neural network.

In general, the operations of method 500 of FIG. 5 may be performed in any suitable order, e.g., consecutively, simultaneously, or a combination thereof, subject to, where applicable, a particular order being necessitated, e.g., by input/output relations. The operations of the method may be repeated in each subsequent iteration, as illustrate by the loop in FIG. 5 from block 540 to block 510. In some embodiments, the block 540 may be performed after several iterations of blocks 510-530, e.g., after all image parts of the image data have been annotated.

Figure 6:
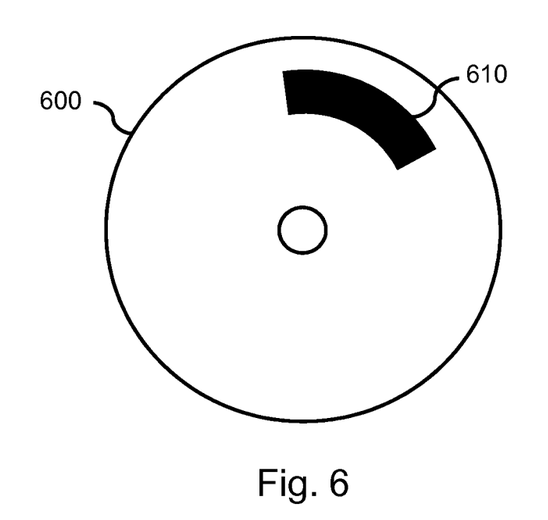
FIG. 6 shows a computer-readable medium comprising instructions for causing a processor system to perform the method.

The method(s) may be implemented on a computer as a computer implemented method, as dedicated hardware, or as a combination of both. As also illustrated in FIG. 6, instructions for the computer, e.g., executable code, may be stored on a computer readable medium 600, e.g., in the form of a series 610 of machine-readable physical marks and/or as a series of elements having different electrical, e.g., magnetic, or optical properties or values. The executable code may be stored in a transitory or non-transitory manner. Examples of computer readable mediums include memory devices, optical storage devices, integrated circuits, servers, online software, etc. FIG. 6 shows an optical disc 600.

In accordance with an abstract of the present application, a system and computer-implemented method may be provided for annotation of image data. A user may be enabled to iteratively annotate the image data. An iteration of said iterative annotation may comprise generating labels for a current image data part based on user-verified labels of a previous image data part, and enabling the user to verify and correct said generated labels to obtain user-verified labels for the current image data part. The labels for the current image data part may be generated by combining respective outputs of a label propagation algorithm, and a neural network trained on user-verified labels and image data and applied to image data of the current image data part. The neural network may be retrained using the user-verified labels and the image data of the current image data part to obtain a retrained neural network.

Examples, embodiments or optional features, whether indicated as non-limiting or not, are not to be understood as limiting the invention as claimed.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or stages other than those stated in a claim. The article "a" or "an" preceding an element does not exclude the presence of a plurality of such elements. Expressions such as "at least one of" when preceding a list or group of elements represent a selection of all or of any subset of elements from the list or group. For example, the expression, "at least one of A, B, and C" should be understood as including only A, only B, only C, both A and B, both A and C, both B and C, or all of A, B, and C. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A system for annotation of image data, the system comprising:
   an input interface configured to access the image data to be annotated;
   a user interface subsystem comprising:
      a user input interface configured to receive user input data from a user input device operable by a user;
      a display output interface configured to provide display data to a display to visualize output of the system;

a processor configured to, using the user interface subsystem, establish a user interface which enables the user to iteratively annotate the image data, wherein an iteration of said iterative annotation comprises:
- the processor generating labels for a current image data part based on user-verified labels of a previous image data part;
- via the user interface, enabling the user to verify and correct said generated labels to obtain user-verified labels for the current image data part;
- wherein the processor is further configured to:
- generate the labels for the current image data part by combining, by weighting, respective outputs of:
  - a label propagation algorithm which propagates the user-verified labels of the previous image data part to the current image data part, and
  - a machine-learned classifier for labeling of image data, wherein the machine-learned classifier is trained on user-verified labels and image data and applied to image data of the current image data part; and
- retrain the machine-learned classifier using the user-verified labels and the image data of the current image data part to obtain a retrained machine-learned classifier.

2. The system according to claim 1, wherein the processor is configured to retrain the machine-learned classifier between iterations of the iterative annotation, or between the iterative annotation of different image data.

3. The system according to claim 1, wherein the processor is configured to adjust the weighting during the iterative annotation of the image data, or between the iterative annotation of different image data.

4. The system according to claim 1, wherein the processor is configured to determine the weighting based on a metric quantifying an annotation accuracy of the label propagation algorithm and/or the machine-learned classifier.

5. The system according to claim 4, wherein the metric quantifies the annotation accuracy based on a difference between i) the output of the label propagation algorithm and/or the output of the machine-learned classifier and ii) the user-corrected labels.

6. The system according to claim 3, wherein the processor is configured to adjust the weighting by increasing a weighting of the output of the machine-learned classifier relative to the output of the label propagation algorithm.

7. The system according to claim 6, wherein the processor is configured to start the weighting of the output of the machine-learned classifier at or substantially at zero at a start of the iterative annotation.

8. The system according to claim 1, wherein the weighting comprises a global weighting per image data part and/or a local weighting per pixel, voxel or other image sub-region.

9. The system according to claim 1, wherein the output of the label propagation algorithm and/or the output of the machine-learned classifier is a probability map, or one or more control points defining a contour.

10. The system according to claim 1, wherein the label propagation algorithm is configured to propagate the user-verified labels of the previous image data part to the current image data part based on a similarity in image data between the previous image data part and the current image data part.

11. The system according to claim 10, wherein the label propagation algorithm is a patch-based label propagation algorithm.

12. A workstation or imaging apparatus comprising the system according to claim 1.

13. A computer-implemented method for annotation of image data, the method comprising:
- accessing the image data to be annotated;
- using a user interface, enabling a user to iteratively annotate the image data, wherein an iteration of said iterative annotation comprises:
  - generating labels for a current image data part based on user-verified labels of a previous image data part;
  - via the user interface, enabling the user to verify and correct said generated labels to obtain user-verified labels for the current image data part;
  - wherein the labels for the current image data part are generated by combining, by weighting, respective outputs of:
    - a label propagation algorithm which propagates the user-verified labels of the previous image data part to the current image data part, and
    - a machine-learned classifier for labeling of image data, wherein the machine-learned classifier is trained on user-verified labels and image data and applied to image data of the current image data part; and
- retraining the machine-learned classifier using the user-verified labels and the image data of the current image data part to obtain a retrained machine-learned classifier.

14. A non-transitory computer readable medium storing instructions that, when executed by one or more processors, cause the one or more processors to:
- access image data to be annotated;
- using a user interface, enable a user to iteratively annotate the image data, wherein an iteration of said iterative annotation comprises:
  - generating labels for a current image data part based on user-verified labels of a previous image data part;
  - via the user interface, enabling the user to verify and correct said generated labels to obtain user-verified labels for the current image data part;
  - wherein the labels for the current image data part are generated by combining, by weighting, respective outputs of:
    - a label propagation algorithm which propagates the user-verified labels of the previous image data part to the current image data part, and
    - a machine-learned classifier for labeling of image data, wherein the machine-learned classifier is trained on user-verified labels and image data and applied to image data of the current image data part; and
  - retraining the machine-learned classifier using the user-verified labels and the image data of the current image data part to obtain a retrained machine-learned classifier.

15. The non-transitory computer readable medium of claim 14, wherein the machine-learned classifier is retrained between iterations of the iterative annotation, or between the iterative annotation of different image data.

16. The non-transitory computer readable medium of claim 14, wherein weighting is adjusted during the iterative annotation of the image data or between the iterative annotation of different image data.

17. The non-transitory computer readable medium of claim 14, wherein the weighting is determined based on a metric quantifying an annotation accuracy of the label propagation algorithm and/or the machine-learned classifier.

18. The non-transitory computer readable medium of claim 17, wherein the metric quantifies the annotation accuracy based on a difference between i) the output of the label propagation algorithm and/or the output of the machine-learned classifier and ii) the user-corrected labels.

19. The non-transitory computer readable medium of claim 16, wherein the weighting is adjusted by increasing a weighting of the output of the machine-learned classifier relative to the output of the label propagation algorithm.

20. The non-transitory computer readable medium of claim 19, wherein the weighting of the output of the machine-learned classifier is started at or substantially at zero at a start of the iterative annotation.

* * * * *